(12) United States Patent
Tang et al.

(10) Patent No.: US 11,440,934 B2
(45) Date of Patent: Sep. 13, 2022

(54) METHOD FOR PREPARING CANGRELOR TETRASODIUM SALT

(71) Applicant: Yabao Pharmaceutical Group Co., Ltd., Shanxi (CN)

(72) Inventors: Fanghui Tang, Shanxi (CN); Jiyu Bao, Shanxi (CN); Junfeng Gao, Shanxi (CN); Zhouhong Tan, Shanxi (CN)

(73) Assignee: Yabao Pharmaceutical Group Co., Ltd., Shanxi (CN)

(*) Notice: Subject to any disclaimer, the term of this patent is extended or adjusted under 35 U.S.C. 154(b) by 232 days.

(21) Appl. No.: 16/768,037

(22) PCT Filed: Dec. 11, 2018

(86) PCT No.: PCT/CN2018/120184
§ 371 (c)(1),
(2) Date: May 28, 2020

(87) PCT Pub. No.: WO2019/114674
PCT Pub. Date: Jun. 20, 2019

(65) Prior Publication Data
US 2021/0371448 A1 Dec. 2, 2021

(30) Foreign Application Priority Data
Dec. 12, 2017 (CN) .......................... 201711318174.2

(51) Int. Cl.
*C07H 19/20* (2006.01)
*C07H 1/04* (2006.01)

(52) U.S. Cl.
CPC .............. *C07H 19/20* (2013.01); *C07H 1/04* (2013.01)

(58) Field of Classification Search
None
See application file for complete search history.

(56) References Cited

FOREIGN PATENT DOCUMENTS

| CN | 1119869 A | 4/1996 |
|---|---|---|
| CN | 1613864 A | 5/2005 |
| CN | 104163843 A | 11/2014 |
| CN | 104592334 A | 5/2015 |
| CN | 105273025 A | 1/2016 |
| CN | 105061431 B | 3/2017 |
| WO | 2017076266 A1 | 5/2017 |
| WO | 2018185715 A1 | 10/2018 |
| WO | 2019092546 A1 | 5/2019 |

OTHER PUBLICATIONS

Jones, Tetrahedron: Asymmetry 16 (2005) 3128-3138. (Year: 2005).*
Cada, Hosp Pharm 2015; 50(10): 922-929. (Year: 2015).*
European Patent Office, International Search Report and Written Opinion, International Application No. 10.18888369.8, dated Jul. 27, 2021, 62 pages.
Office Action for Chinese Patent Application No. 201711318174.2 dated Mar. 3, 2021; 6 pgs.
Ingall, et al., "Antagonists of the Platelet P2T Receptor: A Novel Approach to Antithrombotic Therapy," J. Med. Chem., 1999; 42:213-220.

* cited by examiner

*Primary Examiner* — Layla D Berry
(74) *Attorney, Agent, or Firm* — Umberg Zipser LLP; Jason Tejani

(57) ABSTRACT

The present application relates to a method for prepare a Cangrelor tetrasodium salt, comprising: using N-[2-(methylthio)ethyl]-2-[(3,3,3-trifluoropropyl)sulfonyl]adenosine as a raw material to undergo two steps of reaction to obtain a reaction solution containing the Cangrelor tetrasodium salt; separating and purifying once by C18 silica gel column chromatography so as to obtain a Cangrelor tetrasodium salt pure product. The present application has the advantages of short synthesis route, mild reaction conditions, sufficient reaction, simple operation, high product yield, high purity, and environmental friendliness, and is suitable for large-scale preparation.

18 Claims, No Drawings

METHOD FOR PREPARING CANGRELOR TETRASODIUM SALT

The present application claims the priority of Chinese Patent Application No. 201711318174.2, with the title of "CANGRELOR TETRASODIUM PREPARATION METHOD", filed on Dec. 12, 2017 before the China National Intellectual Property Administration, which is incorporated herein by reference in its entirety.

FIELD OF THE INVENTION

The present application relates to the technical field of chemical synthesis of drugs. Specifically, it relates to a method for preparing Cangrelor tetrasodium salt.

BACKGROUND OF THE INVENTION

Cangrelor tetrasodium, a P2Y12 receptor inhibitor, was invented and produced by Astra7eneca and licensed to Medicines for research and development. The US Food and Drug Administration (FDA) approved the marketing of the intravenous injection for Cangrelor tetrasodium salt under the trade name of Kengreal on Jun. 22, 2015, which was used for reducing events of thrombotic cardiovascular disease in patients with percutaneous coronary intervention (PCI). Unlike antiplatelet drugs such as Clopidogrel and Prasugrel, Cangrelor is a non-thienopyridine adenosine triphosphate analog, which can directly act on P2Y12 platelet receptors and rapidly inhibit platelet aggregation. It has the advantages of taking effect quickly, acting reversibly, fast metabolism and less risk of bleeding.

The chemical name of Cangrelor tetrasodium salt is: N-[2-(methylthio)ethyl]-2-[(3,3,3-trifluoropropyl)thio]-5'-adenine nucleotide, bearing a dichloromethylene diphosphate monoanhydride, tetrasodium salt, and the structural formula thereof is as follows:

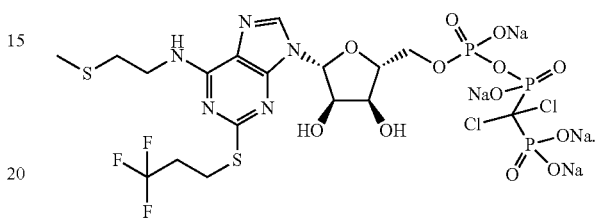

A method of preparing Cangrelor tetrasodium salt is reported in the reference *J. Med. Chem.* 1999, 12, 213-220, and the synthetic route is as follows:

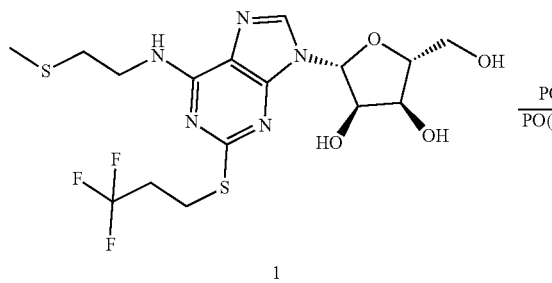

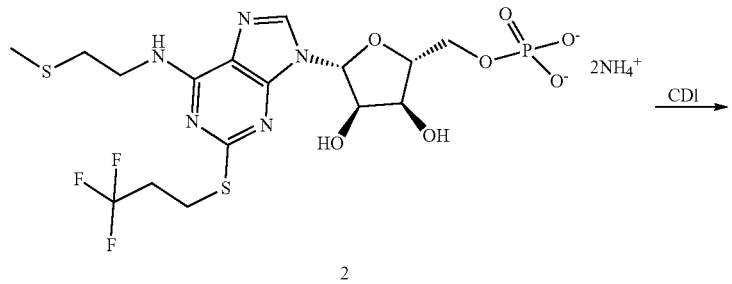

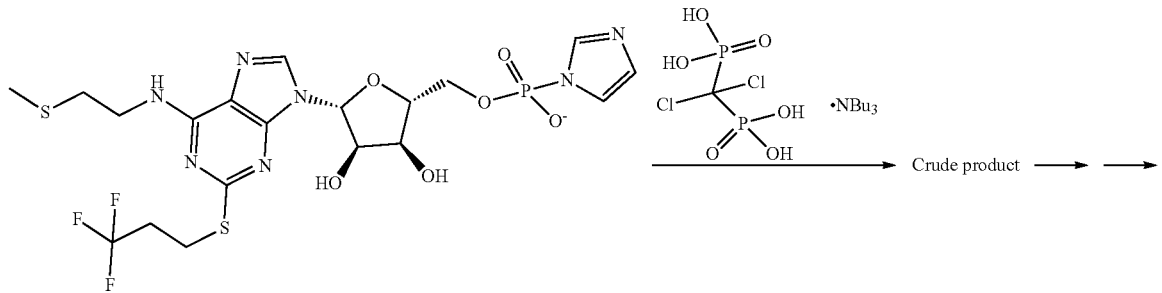

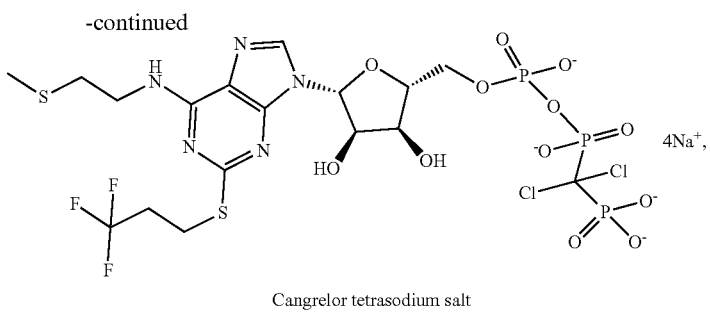

Cangrelor tetrasodium salt wherein, the compound 1 was reacted with phosphorus oxychloride, and the reaction solution was purified by a chromatography column Dowex 50WX8 (H+ form), and eluted with aqueous ammonia. The eluate was lyophilized and concentrated to obtain a compound 2. The compound 2 contained water which was removed by azeotropic dehydration with pyridine, and was reacted with CDI in DMF to obtain a compound 3. The compound 3 was then reacted with tri-n-butylamine dichloromethylene diphosphate to obtain a crude product. The crude product was purified using dextran gel, DEAE-Sephadex and eluted with triethylammonium bicarbonate or ammonium bicarbonate solution. The eluate was lyophilized, concentrated and detected. The eluate containing mainly the product was collected and lyophilized to obtain Cangrelor ammonium salt, which was transformed, separated, washed, and lyophilized to obtain Cangrelor tetrasodium salt. The preparation method includes a long route and a complicated process, requiring multiple purifications and lyophilizations. The purification using dextran gel has poor effect. The yield from a compound 1 to Cangrelor ammonium salt is only 4%. In addition, the large amount of organic solvent will lead to environmental problems.

CN1613864A discloses a method for purifying and preparing nucleoside triphosphate trisodium salt (i.e. Cangrelor trisodium salt) to solve the problem that unreacted raw materials and products cannot be effectively separated, and the reaction formula is as follows:

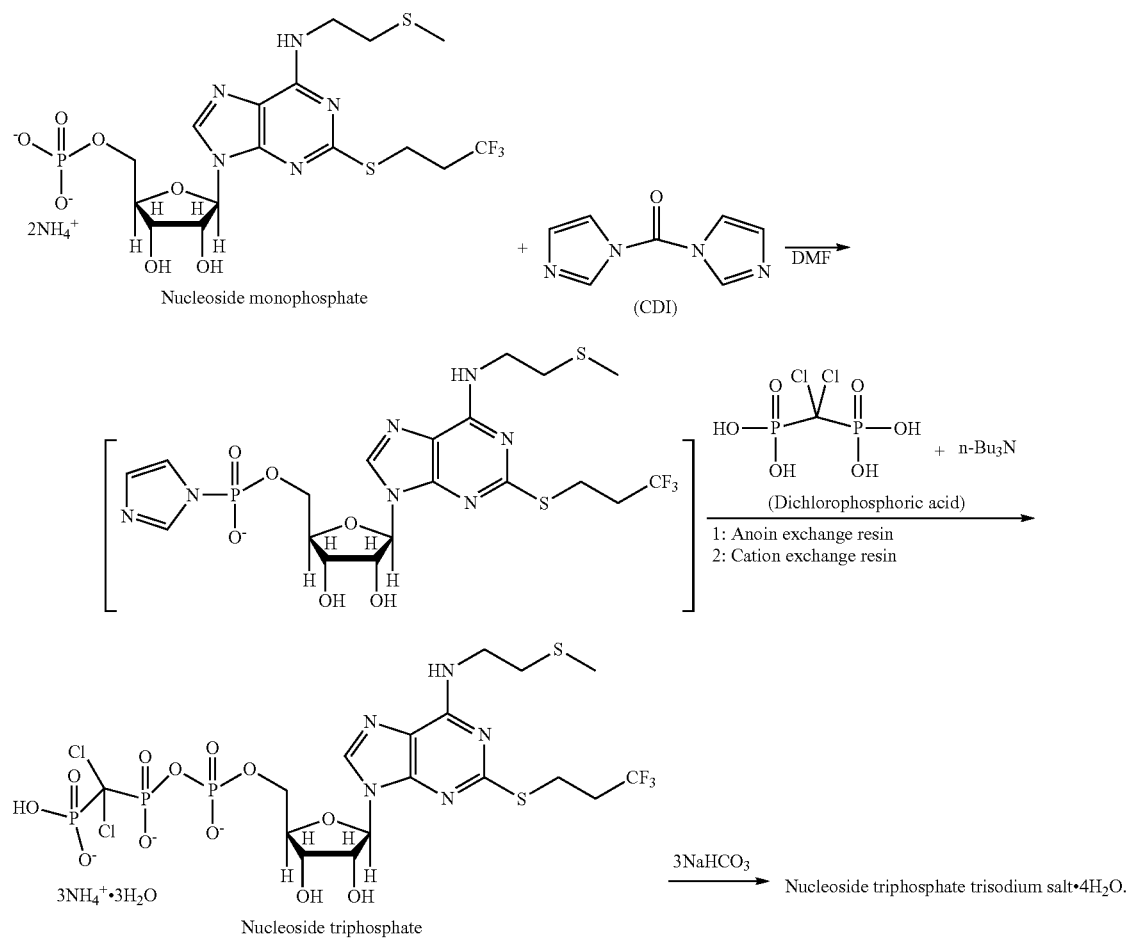

The main steps include: using nucleoside monophosphate ammonium salt as raw material to obtain a process reaction solution containing Cangrelor according to the synthesis method of *J. Med. Chem.* 1999, 12, 213-220, wherein, firstly, the process reaction solution containing Cangrelor was separated roughly by anion exchange resin and eluted with an aqueous ammonium bicarbonate solution, and the eluate was lyophilized to obtain a small amount of pure product as nucleoside triphosphate ammonium salt (i.e., Cangrelor ammonium salt) and a large amount of impurities. The impurities contained 14-18% of unreacted raw material nucleoside monophosphate ammonium salt. The impurities were separated and purified by a strong acid cation exchange resin with large pores. The effluent was reacted with ammonium bicarbonate to obtain an eluate comprising nucleoside triphosphate ammonium salt, and the eluate was lyophilized; and the raw materials left in the resin were recovered. The pure products of the nucleoside triphosphate ammonium salt were combined and replaced with an aqueous sodium bicarbonate solution to obtain a nucleoside triphosphate trisodium salt (i.e., Cangrelor trisodium salt), and the nucleoside triphosphate trisodium salt was lyophilized. Although the preparation method increases the yield of Cangrelor ammonium salt to 50%-58%, there are still many problems, including: incomplete reaction, wherein the reaction solution contains a large amount of unreacted raw materials; formation of deliquescent Cangrelor ammonium salt as an intermediate; the complex process, which increases the times of purifications and lyophilizing, is time-consuming and labor-consuming, and produces significant amount of wastes, and thus is not conducive to large-scale preparation.

U.S. Pat. No. 9,295,687B1 reports impurities of Cangrelor, and the structural formula thereof as follows:

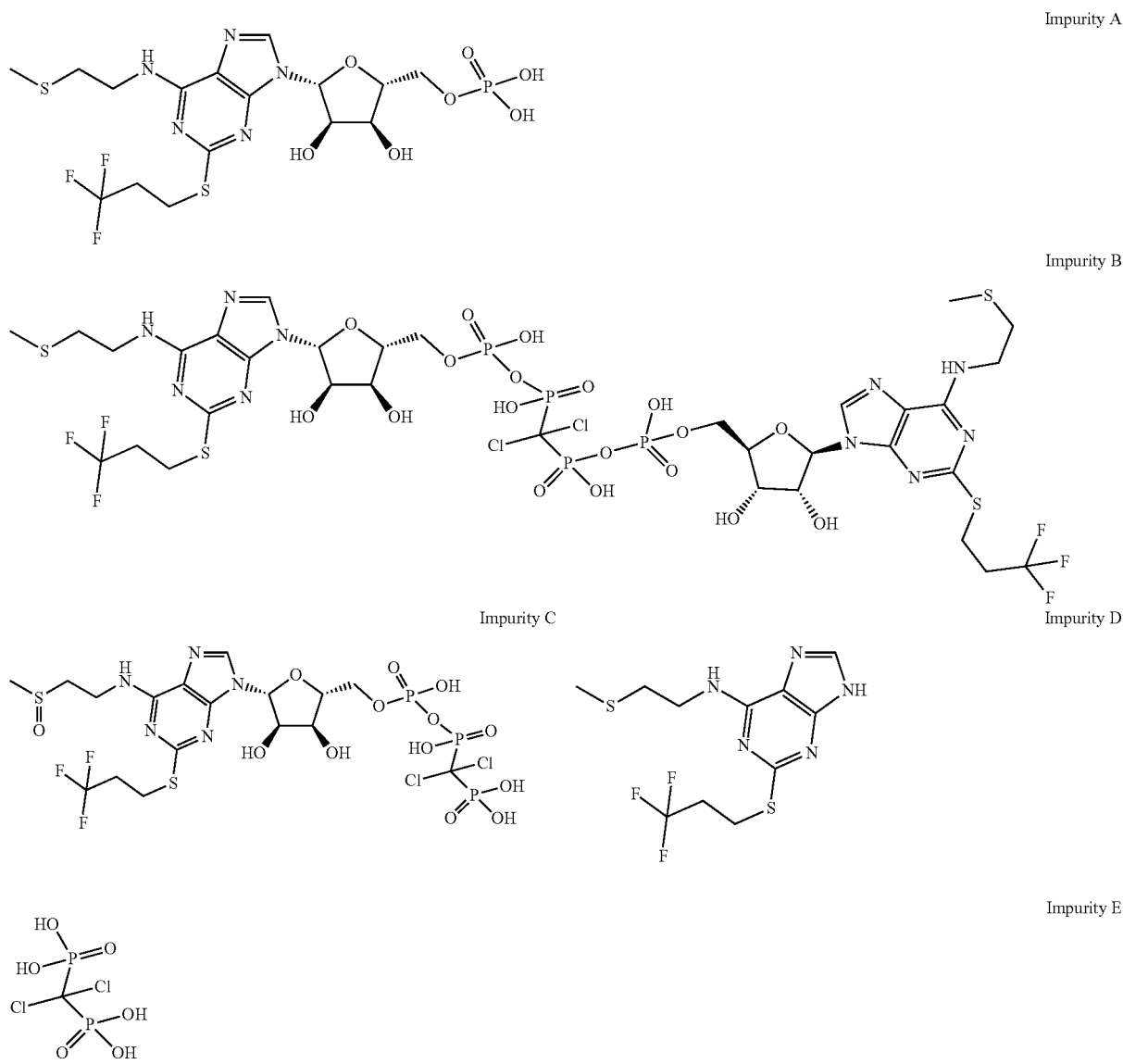

The ICH guideline of API requires that the unknown single impurity in the API is less than 0.1%. The inventors found that the Cangrelor sodium salt obtained according to the preparation method of the previous literatures has high impurity content, for example, the content of impurity A is greater than 2%, which does not meet the quality requirements of API.

SUMMARY OF THE INVENTION

In view of the deficiencies in the prior art, the purpose of the present application is to provide a new method for preparing Cangrelor tetrasodium salt, which simplifies the operation by optimizing the synthetic route and process, improves the yield and purity of the product, and satisfies the demand of large-scale preparation.

According to the purpose of the present application, the technical solution of the present application is as follows:

A method for preparing Cangrelor tetrasodium salt, comprising the following steps:

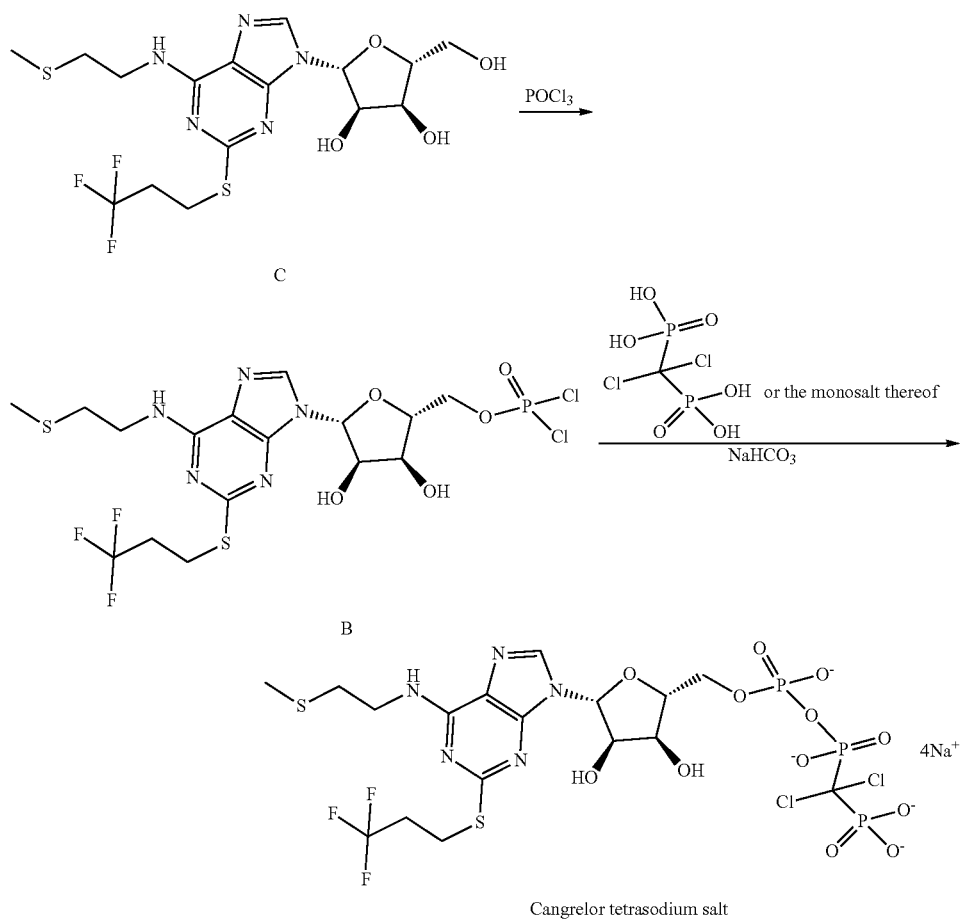

step (1), reacting a compound C with phosphorus oxychloride in an organic solvent to obtain a reaction solution containing a compound B;
step (2), reacting the reaction solution containing the compound B obtained in step (1) with clodronic acid or a monosalt thereof in the presence of an acid-binding agent, and then with sodium bicarbonate to obtain a reaction solution containing Cangrelor tetrasodium salt; and
step (3), obtaining Cangrelor tetrasodium salt from the reaction solution containing Cangrelor tetrasodium salt obtained in step (2); preferably, separating and purifying the reaction solution containing Cangrelor tetrasodium salt obtained in step (2) by column chromatography, eluting with an eluent, collecting an eluate of Cangrelor tetrasodium salt with a HPLC purity≥99.5%, and lyophilizing to obtain Cangrelor tetrasodium salt; more preferably, the column chromatography is C18 silica gel column chromatography; most preferably, separating and purifying the reaction solution containing Cangrelor tetrasodium salt obtained in step (2) by column chromatography once, eluting with an eluent to obtain an eluate of Cangrelor tetrasodium salt with a HPLC purity≥99.5%, and lyophilizing to obtain Cangrelor tetrasodium salt.

In the present application, the chemical name of the starting material compound C is N-[2-(methylthio)ethyl]-2-[(3,3,3-trifluoropropyl)thio]adenosine, CAS NO.: 163706-58-9. the compound C may be commercially available, or obtained according to the preparation methods in the literatures, for example, *J. Med. Chem.* 1999, 12, 213-220.

Preferably, the organic solvent in step (1) is selected from the group consisting of acetonitrile, triethyl phosphate, and trimethyl phosphate, or any combination thereof.

Preferably, the molar ratio of the compound C to the phosphorus oxychloride in step (1) is 1:1-1:3.

In step (1), the compound C and the phosphorus oxychloride can be reacted in the absence of a base or in the presence of a base, preferably reacted in the presence of a base. Preferably, the base is selected from the group consisting of 1,8-bis(dimethylamino)naphthalene, triethylamine, tri-n-propylamine, tri-n-butylamine and diisopropylethylamine More preferably, the molar ratio of the compound C to the base is 1:0.1-1:2.

Preferably, the reaction in step (1) is performed at a temperature of −30 to 20° C. for 1-24 hours. More preferably, the reaction in step (1) is performed at a temperature of −10 to 10° C. for 3-10 hours.

According to the present application, after step (1) is completed, the resulting reaction solution containing the compound B can be used directly in the next reaction without treatment, which greatly simplifies the process.

According to one of the embodiments of the present application, the definition of the acid-binding agent in step (2) is common knowledge to those skilled in the art. Preferably, the acid-binding agent in step (2) is selected from the group consisting of triethylamine, tri-n-propylamine, tri-n-butylamine, and N,N-diisopropylethylamine, or any combination thereof. More preferably, the molar ratio of the compound C to the acid-binding agent is 1:2-1:8.

According to the present application, in step (2), the molar ratio of the compound C to the clodronic acid or the monosalt thereof is 1:1.1 to 1:3.5. Preferably, the molar ratio of the compound C to the clodronic acid or the monosalt thereof is 1:1.4-1:2. The monosalt of clodronic acid can be selected from the group consisting of monosalt of tri-n-butylamine dichloromethylene diphosphate, monosodium salt of clodronic acid, and monopotassium salt of clodronic acid, or any combination thereof. Most preferably, the monosalt of clodronic acid is monosalt of tri-n-butylamine dichloromethylene diphosphate.

According to the present application, in step (2), the clodronic acid or the monosalt thereof may be added in batches in solid form, or may be added in batches after formulating into a solution using the organic solvent described in step (1).

According to the present application, in step (2), the molar ratio of the compound C to the sodium bicarbonate is 1:10 to 1:30. Preferably, the molar ratio of the compound C to sodium bicarbonate is 1:15 to 1:20. In step (2), the sodium bicarbonate can be added in batches in solid form, or in an aqueous sodium bicarbonate solution. The mass concentration of the sodium bicarbonate solution is generally from 1.0% to the concentration of its saturated solution, preferably 5%-9%.

According to one of the embodiments of the present application, in step (2), the reaction solution containing the compound B obtained in step (1) is reacted with clodronic acid or the monosalt thereof at the temperature of −10 to 30° C. for 1-5 hours. In step (2), the resultant is further reacted with sodium bicarbonate at the temperature of 10-40° C. for 10-40 hours.

According to the preparation method provided in the present application, at the end of step (2), the reaction solution containing Cangrelor tetrasodium salt is obtained. The inventor found that, by HPLC detection, the reaction solution mainly contains about 80-85 mol % of Cangrelor tetrasodium salt, and only about 2-5 mol % of disodium salt of impurity A (the structural formula is shown below).

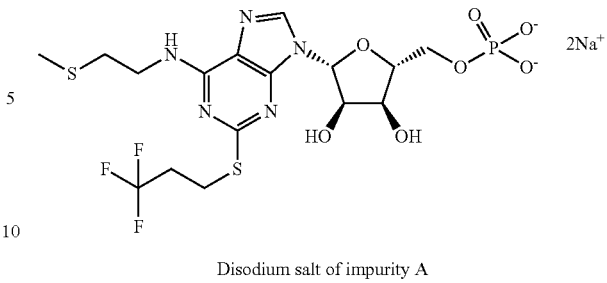

Disodium salt of impurity A

In step (3), the "C18 silica gel" refers to octadecylsilyl silica gel (abbreviated as ODS). Since C18 silica gel uses silica gel as a matrix to bond octadecyl functional groups, it has high carbon content and hydrophobicity. In the reversed-phase separation mode using C18 silica gel as the column chromatography filler, non-polar or hydrophobic compounds are strongly retained, while polar compounds are weakly retained. Thus the resultant can pass through the column faster to achieve separation and purification of the components.

C18 silica gel fillers are commercially available, such as DAISOGEL ODS, YMC ODS, GH GEL ODS, COSMOS-ILC18, Fuji Chromatorex C18, Silicycle ODS, SKR-10, SEPAX C18, etc. The particle sizes of available fillers are from 1.8 microns to 300 microns or more.

According to the present application, in step (3), in view of the cost and efficiency of large-scale production, the particle size of the C18 silica gel filler is preferably selected from 20-150 microns. More preferably, the particle size of the C18 silica gel filler is 40-100 microns.

According to the present application, in step (3), in view of safety and environmental protection, the eluent is selected from the group consisting of 0.1 v/v %-10 v/v % of aqueous methanol solution, and 0.1 v/v %-10 v/v % of aqueous acetonitrile solution and water. Preferably, the eluent is water. The "water" mentioned in the present application refers to the water used in the pharmaceutical industry, which complies with the requirements of the "Good Manufacturing Practice". The mode of eluting can be gradient elution or isocratic elution.

According to the present application, in step (3), the mass ratio of the C18 silica gel filler to the compound C is 35:1-130:1. Preferably, the mass ratio of the C18 silica gel filler to the compound C is 60:1-90:1.

Alternatively, in step (3), the mechanical impurities of the reaction solution containing Cangrelor tetrasodium salt are removed by using conventional methods in the art, such as filtration, before the reaction solution passes through C18 silica gel column chromatography.

Alternatively, in step (3), the part impurities of the reaction solution containing Cangrelor tetrasodium salt are extracted and removed before the reaction solution passes through C18 silica gel column chromatography. The selection of extractants is a common operation for those skilled in the art, which will not be described herein.

The inventor further studied and found that the replacement of C18 silica gel in the column chromatography in step (3) by other fillers with physical and chemical properties similar to C18 silica gel can also achieve good separation and purification results.

According to the present application, a method for preparing Cangrelor tetrasodium salt is provided, which comprises the following steps:

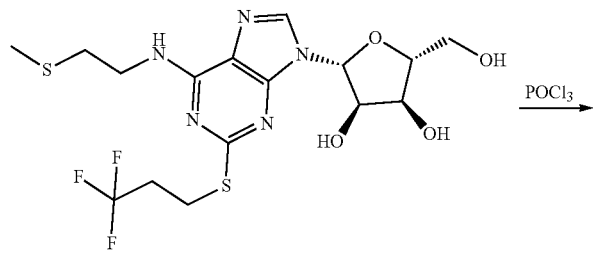

C

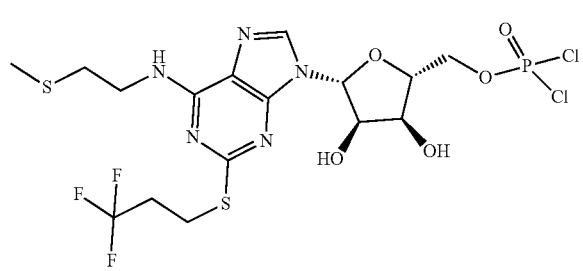

B

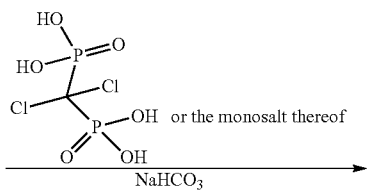

or the monosalt thereof

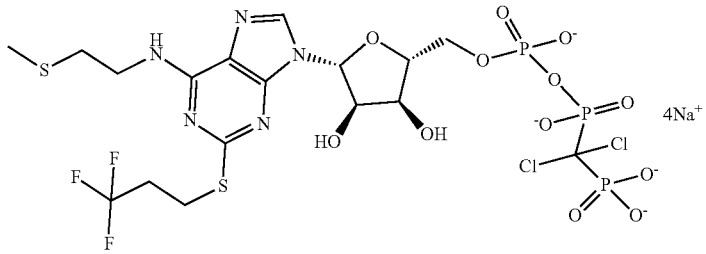

Cangrelor tetrasodium salt step (1), reacting a compound C with phosphorus oxychloride in an organic solvent at a temperature of −30 to 20° C. for 1-24 hours to obtain a reaction solution containing a compound B, wherein the organic solvent is selected from the group consisting of acetonitrile, triethyl phosphate and trimethyl phosphate, and the molar ratio of the compound C to the phosphorus oxychloride is 1:1-1:3;

step (2), reacting the reaction solution containing the compound B obtained in step (1) with clodronic acid or the monosalt thereof in the presence of an acid-binding agent at a temperature of −10 to 30° C. for 1-5 h, and then with sodium bicarbonate at a temperature of 10-40° C. for 10-40 hours to obtain a reaction solution containing Cangrelor tetrasodium salt,
wherein, the acid-binding agent is selected from the group consisting of triethylamine, tri-n-propylamine, tri-n-butylamine and N,N-diisopropylethylamine, the molar ratio of the compound C to the acid-binding agent is 1:2-1:8, the monosalt of clodronic acid is selected from the group consisting of monosalt of tri-n-butylamine dichloromethylene diphosphate, monosodium salt of clodronic acid, and monopotassium salt of clodronic acid. The molar ratio of the compound C to the clodronic acid or the monosalt thereof is 1:1.1-1:3.5, and the molar ratio of the compound C to the sodium bicarbonate is 1:10-1:30; and step (3), separating and purifying the reaction solution containing Cangrelor tetrasodium salt obtained in step (2) by C18 silica gel column chromatography, eluting with a eluent, collecting an eluate of Cangrelor tetrasodium salt with a HPLC purity≥99.5% and lyophilizing to obtain Cangrelor tetrasodium salt;
wherein, the particle sizes of the C18 silica gel fillers are 20-150 microns, the mass ratio of the C18 silica gel fillers to the compound C is 35:1-130:1, and the eluent is selected from the group consisting of 0.1 v/v %-10 v/v % of aqueous methanol solution, 0.1 v/v %-10 v/v % of aqueous acetonitrile solution and water.

According to the present application, wherein:
preferably, the reaction in step (1) is performed at the temperature of −10 to 10° C. for 3-10 hours;
preferably, in step (2), the molar ratio of the compound C to the clodronic acid or the monosalt thereof is 1:1.4 to 1:2;
preferably, the molar ratio of the compound C to the sodium bicarbonate is 1:15-1:20;
preferably, in step (3), the particle size of the C18 silica gel filler is 40-100 microns; preferably, the mass ratio of the C18 silica gel fillers to the compound C is 60:1-90:1, and preferably, the eluent is water.

Compared with the prior art, the present application has the following significant advantages: the synthetic route of the present application is short, the reaction solution containing Cangrelor tetrasodium salt can be obtained through a one-pot process in two-step, starting with N-[2-(methylthio)ethyl]-2-[(3,3,3-trifluoropropyl)thio]adenosine (the compound C). The reaction is sufficient, without the formation of Cangrelor ammonium salt intermediate which is then converted into the salt. The reaction conditions are mild and the operation is simple. The post-treatment only comprises separating and purifying once by C18 silica gel column chromatography. The eluent is water or an aqueous solution of a low-concentration organic solvent with water as the main component. The waste is less and the cost is low. The product has a HPLC purity≥99.5%, which reaches the quality requirements of API, the yield is more than 70%, and the method is suitable for large-scale production.

DETAILED DESCRIPTION OF THE INVENTION

The present application is further defined with reference to the following examples, which describe in detail the preparation method of the present application. It is obvious to those skilled in the art that a plurality of changes to the preparation conditions can be implemented without departing from the scope of the present application.

The reagents used in the examples are commercially available unless otherwise specified.

The examples are carried out at room temperature (10° C. to 30° C.) unless otherwise specified.

The instruments and equipment used includes:
Lyophilizer (Bilang Instrument Manufacturing Co., Ltd., Shanghai),
AV-400 NMR instrument (Bruker, German),
LC-20AT HPLC instrument (Shimadzu Corporation, Japan).
HPLC Detection Conditions:
InertsilODS-2 column C18, specification: 5 μm, 4.6 mm×250 mm
Mobile phase A: 0.05M amine phosphate solution (pH is adjusted to 7.2 with acetic acid and triethylamine)
Mobile phase B: acetonitrile
HPLC Gradient:

| Time (min) | 0 | 30 | 35 | 45 |
| --- | --- | --- | --- | --- |
| Mobile phase A (%) | 80 | 50 | 80 | 80 |
| Mobile phase B (%) | 20 | 50 | 20 | 20 |

Flow rate: 1 ml/min
Duration: 45 min
UV absorption wavelength: 242 nm

Example 1

The compound C 4.7 g (10 mmol), triethyl phosphate 90 mL and 1,8-bis(dimethylamino)naphthalene 2.1 g (10 mmol) were added into a 500 ml four-necked flask, cooled to −10° C., and phosphorus oxychloride 3.1 g (20 mmol) was added dropwise. After the dropwise addition, the reaction was performed at a constant temperature for 20 hours to obtain a reaction solution containing the compound B.

Tri-n-butylamine 10.2 g (55 mmol), clodronic acid 3.7 g (15 mmol) and triethyl phosphate 50 ml were mixed and added to the above reaction solution containing the compound B, and stirred at room temperature for 2 hours. Then, 315 g of 8% by mass of aqueous sodium bicarbonate solution was added and stirred at room temperature for 12 hours.

After filtration, the filtrate was separated and purified by a chromatographic column equipped with 420 g YMC ODS-A C18 silica gel filler (100 microns in particle size), isocratically eluted with 5 v/v % of aqueous methanol solution at a flow rate of 2.0 L/h. The eluate was collected in stages and detected by HPLC, and the eluate of Cangrelor tetrasodium salt with a HPLC purity≥99.5% was combined and lyophilized to obtain 6.1 g of white powdered solid as Cangrelor tetrasodium salt.

The molar yield of Cangrelor tetrasodium salt was 71%, the HPLC purity was 99.91%, the amount of disodium salt of impurity A was 0.03%, the amount of impurity C was 0.02%, and impurities B, D and E were not detected. NMR data: $^1$H-NMR δ(D$_2$O): 8.23 (1H, s), 5.95 (1H, d, J=5.6 Hz), 4.65 (1H, m), 4.49 (1H, m), 4.28 (1H, m), 4.17 (2H, m), 3.67 (1H, s), 3.21 (2H, t, J=7.6 Hz), 2.72 (2H, t, J=6.8 Hz), 2.58 (2H, m), 2.01 (3H, s).

Example 2

The compound C 4.7 g (10 mmol), triethyl phosphate 60 mL, acetonitrile 50 ml, and diisopropylethylamine 2.6 g (20 mmol) were added into a 500 ml four-necked flask, cooled to 0° C., and phosphorus oxychloride 2.3 g (15 mmol) was added dropwise. After the dropwise addition, the reaction was performed at a constant temperature for 5 hours to obtain a reaction solution containing the compound B.

Tri-n-butylamine 13.0 g (70 mmol), clodronic acid 7.4 g (30 mmol) and triethyl phosphate 50 ml were mixed and added to the above reaction solution containing the compound B, and stirred at 0° C. for 4 hours. Then, 126 g of 10% by mass of aqueous sodium bicarbonate solution was added and the reaction was stirred at 30° C. for 28 hours.

After filtration, the filtrate was extracted with 200 ml of methyl tert-butyl ether, and the aqueous phase was separated and purified by a chromatographic column equipped with 280 g YMC ODS-A C18 silica gel filler (50 microns in particle size), isocratically eluted with 5 v/v % of aqueous acetonitrile solution at a flow rate of 2.0 L/h. The eluate was collected in stages and detected by HPLC, and the eluate of Cangrelor tetrasodium salt with HPLC purity≥99.5% was combined and lyophilized to obtain 6.2 g of white powdered solid as Cangrelor tetrasodium salt.

The molar yield of Cangrelor tetrasodium salt was 72%, the HPLC purity was 99.94%, the amount of disodium salt of impurity A was 0.02%, the amount of impurity C was 0.02%, and impurities B, D and E were not detected.

Example 3

The compound C 4.7 g (10 mmol), triethyl phosphate 90 mL, and diisopropylethylamine 1.3 g (10 mmol) were added into a 500 ml four-necked flask, cooled to 10° C., and phosphorus oxychloride 3.1 g (20 mmol) was added dropwise. After the dropwise addition, the reaction was performed at a constant temperature for 1 hour to obtain a reaction solution containing the compound B.

Tri-n-propylamine 4.3 g (30 mmol), clodronic acid 4.9 g (20 mmol, 2 eq) and triethyl phosphate 20 ml were mixed and added to the above reaction solution containing the compound B, and stirred at room temperature for 2 hours. Then, 500 g of 5% by mass of aqueous sodium bicarbonate solution was added and stirred at 40° C. for 20 hours.

After filtration, the filtrate was separated and purified by a chromatographic column equipped with 165 g DAISO-GEL ODS-BP C18 silica gel filler (50 microns in particle size), eluted with purified water at a flow rate of 2.0 L/h. The eluate was collected in stages and detected by HPLC, and the eluate of Cangrelor tetrasodium salt with a HPLC purity≥99.5% was combined and lyophilized to obtain 6.6 g of white powdered solid as Cangrelor tetrasodium salt.

The molar yield of Cangrelor tetrasodium salt was 76%, the HPLC purity was 99.79%, the amount of disodium salt of impurity A was 0.05%, the amount of impurity C was 0.04%, and impurities B, D and E were not detected.

Example 4

The compound C 4.7 g (10 mmol), acetonitrile 90 ml and 1,8-bis(dimethylamino)naphthalene 0.54 g (2.5 mmol) were added into a 500 ml four-necked flask, cooled to −10° C., and phosphorus oxychloride 4.6 g (30 mmol) was added dropwise. After the dropwise addition, the reaction was performed at a constant temperature for 10 hours to obtain a reaction solution containing the compound B.

Triethylamine 5.1 g (50 mmol), monosalt of tri-n-butylamine dichloromethylene diphosphate 6.5 g (15 mmol), and acetonitrile 50 ml were mixed and added to the above reaction solution containing the compound B, and stirred at room temperature for 5 hours. Then, 84 g of 10% by mass of aqueous sodium bicarbonate solution was added and stirred at room temperature for 20 hours.

After filtration, the filtrate was separated and purified by a chromatographic column equipped with 200 g YMC ODS-AQ C18 silica gel filler (20 microns in particle size), eluted with deionized water at a flow rate of 2.0 L/h. The eluate was collected in stages and detected by HPLC, and the eluate of Cangrelor tetrasodium salt with a HPLC purity≥99.5% was combined and lyophilized to obtain 6.1 g of white powdered solid as Cangrelor tetrasodium salt.

The molar yield of Cangrelor tetrasodium salt was 71%, the HPLC purity was 99.91%, the amount of disodium salt of impurity A was 0.03%, the amount of impurity C was 0.02%, and impurities B, D and E were not detected.

Example 5

The compound C 4.7 g (10 mmol), triethyl phosphate 90 mL and 1,8-bis(dimethylamino)naphthalene 2.1 g (10 mmol) were added into a 500 ml four-necked flask, cooled to −10° C., and phosphorus oxychloride 3.1 g (20 mmol) was added dropwise. After the dropwise addition, the reaction was performed at a constant temperature for 5 hours to obtain a reaction solution containing the compound B.

Tri-n-butylamine 10.2 g (55 mmol), clodronic acid 3.7 g (15 mmol) and triethyl phosphate 50 ml were mixed, added to the above reaction solution containing the compound B, and stirred at room temperature for 2 hours. Then, 200 g of 8% by mass of aqueous sodium bicarbonate solution was added and stirred at room temperature for 20 hours.

After filtration, the filtrate was separated and purified by a chromatographic column equipped with 350 g FUJI CHROMATOREXC18 SMB100-20/45 C18 silica gel filler (20-45 microns in particle size), eluted with 2 L of 1 v/v % of aqueous methanol solution, and eluted with deionized water at a flow rate of 2.0 L/h. The eluate was collected in stages and detected by HPLC, and the eluate of Cangrelor tetrasodium salt with a HPLC purity≥99.5% was combined and lyophilized to obtain 6.5 g of white powdered solid as Cangrelor tetrasodium salt.

The molar yield of Cangrelor tetrasodium salt was 75%, the HPLC purity was 99.96%, the amount of disodium salt of impurity A was 0.02%, the amount of impurity C was 0.02%, and impurities B, D and E were not detected.

Example 6

The compound C 470 g (1 mol), triethyl phosphate 4.7 mL and 1,8-bis(dimethylamino)naphthalene 214 g (1 mol) were added into a 20 L reaction kettle, cooled to −10° C., and phosphorus oxychloride 230 g (1.5 mol) was added dropwise. After the dropwise addition, the reaction was performed at a constant temperature for 3 hours until HPLC central control showed that the content of the compound C is less than 5% to obtain a reaction solution containing the compound B.

Tri-n-butylamine 740 g (4 mol), clodronic acid 490 g (2 mol) and triethyl phosphate 5 L were mixed, added to the above reaction solution containing the compound B, and stirred at 25-30° C. for 2 hours.

In another reaction kettle, 21 kg of 8% by mass of aqueous sodium bicarbonate solution was prepared, and the above reaction solution was added dropwise to the aqueous sodium bicarbonate solution with stirring, stirred at 30-40° C. for 30 hours.

After filtration, the filtrate was separated and purified by a chromatographic column equipped with 30 kg YMC ODS-A C18 silica gel filler (75 microns in particle size), and eluted with deionized water. The eluate was collected in stages and detected by HPLC, and the eluate of Cangrelor tetrasodium salt with a HPLC purity≥99.5% was combined and lyophilized to obtain 635 g of white powdered solid as Cangrelor tetrasodium salt.

The molar yield of Cangrelor tetrasodium salt was 73.5%, the HPLC purity was 99.88%, the amount of disodium salt of impurity A was 0.03%, the amount of impurity C was 0.04%, and impurities B, D and E were not detected. NMR data: $^1$H-NMR δ(D$_2$O): 8.23 (1H, s), 5.95 (1H, d, J=5.6 Hz), 4.65 (1H, m), 4.49 (1H, m), 4.28 (1H, m), 4.17 (2H, m), 3.67 (1H, s), 3.21 (2H, t, J=7.6 Hz), 2.72 (2H, t, J=6.8 Hz), 2.58 (2H, m), 2.01 (3H, s).

Example 7

The compound C 4.7 g (10 mmol) and triethyl phosphate 90 mL were added into a 500 ml four-necked flask, cooled to −10° C., and phosphorus oxychloride 3.1 g (20 mmol) was added dropwise. After the dropwise addition, the reaction was performed at a constant temperature for 20 hours to obtain a reaction solution containing the compound B.

Tri-n-butylamine 10.2 g (55 mmol), clodronic acid 3.7 g (15 mmol) and triethyl phosphate 50 ml were mixed and added to the above reaction solution containing the compound B, and stirred at room temperature for 2 hours. Then, 315 g of 8% by mass of aqueous sodium bicarbonate solution was carefully added and stirred at room temperature for 12 hours.

After filtration, the filtrate was separated and purified by a chromatographic column equipped with 420 g YMC ODS-A C18 silica gel filler (100 microns in particle size), isocratically eluted with 5 v/v % of aqueous methanol solution at a flow rate of 2.0 L/h. The eluate was collected in stages and detected by HPLC, and the eluate of Cangrelor tetrasodium salt with a HPLC purity≥99.5% was combined and lyophilized to obtain 6.3 g of white powdered solid as Cangrelor tetrasodium salt.

The molar yield of Cangrelor tetrasodium salt was 73%, the HPLC purity was 99.91%, the amount of disodium salt of impurity A was 0.03%, the amount of impurity C was 0.02%, and impurities B, D and E were not detected.

Comparative Example 1 (Preparation of Cangrelor Trisodium Salt According to CN1613864A)

1.85 g of tri-n-butylamine was dissolved in 150 mL of pyridine, and 5.83 g of nucleoside monophosphate ammonium salt was added, stirred to dissolve, and vacuum distilled at 40° C. After removing water by azeotropic dehydration, 120 mL DMF, 8.1 g CDI were added, and the reaction was performed for 16 hours under stirring. Then, 2.46 g methanol was added, stirred for 1 hour, and a solution of 13.92 g of clodronic acid, 10.56 g of tri-n-butylamine and 350 mL of DMF were added dropwise, and stirred at room temperature for 26 hours, filtered to remove insoluble impurities. The filtrate was vacuum-dried to remove the solvent at 60° C. 200 mL of purified water was added to dissolve. The resultant was separated and purified by the anion exchange resin DEAE-Sephadex A-100, eluted sequentially with 5 L deionized water, 2.5 L of 0.1 M aqueous ammonium bicarbonate solution, 2.5 L of 0.2 M aqueous ammonium bicarbonate solution, and finally 0.3 M aqueous ammonium bicarbonate solution, and detected by HPLC. 7.2 L of eluate containing Cangrelor was collected and lyophilized to obtain 5.1 g of Cangrelor triammonium salt, molar yield: 56.7%, HPLC purity: 91.3%, nucleoside monophosphate ammonium salt (impurity A ammonium salt): 7.1%, and impurity C: 0.6%.

Comparative Example 2 (Synthesis of Cangrelor Tetrasodium Salt According to the Literature *J. Med. Chem.* 1999, 12, 213-220)

5.17 g (11 mmol) of the compound C was dissolved in 120 mL triethyl phosphate, cooled to 0° C., and 6.6 g phosphorus oxychloride (43 mmol) was added dropwise. After the dropwise addition, the reaction was performed at a constant temperature for 5 hours. The resultant was poured into 1 L ice cold water containing 14.5 g sodium bicarbonate. The mixture was stirred for 45 minutes, extracted with ether 200 mL×2. The aqueous phase was passed through a chromatographic column Dowex 50WX8 (H⁺ form), eluted with aqueous ammonia. The eluate was lyophilized to obtain the compound nucleoside monophosphate ammonium salt.

The ammonium salt obtained in the previous step was added to a reaction bottle, and 1.57 g tri-n-butylamine and 50 mL pyridine were added, evaporate to dryness under reduced pressure, which was repeated three times, each time with 50 mL pyridine. 100 mL DMF and 6.6 g CDI were added to the residue. The reaction was performed for 4 hours under stirring. 2 g methanol was added, stirred for further 30 minutes, and 100 mL DMF containing 21 g tri-n-butylamine dichloromethylene diphosphate were added, reacted for 18 hours, and filtered. The solvent was evaporated to dryness under reduced pressure, and the residue was dissolved in 100 mL of deionized water, separated and purified by DEAE-Sephadex-A25, eluted by gradient elution with 0-0.6 M aqueous ammonium bicarbonate. The eluate was collected in stages and monitored by HPLC. The eluates containing Cangrelor component were combined and lyophilized to obtain the ammonium salt, which was dissolved in 20 mL methanol. 300 mL of 1 M sodium iodide in acetone was added dropwise, stirred at room temperature for 3 hours, filtered by filter-press with nitrogen, washed with acetone, and the filter cake was dissolved with 100 mL purified water, lyophilized to obtain 910 mg Cangrelor tetrasodium salt, with a molar yield of 9%, a HPLC purity of 96.5%, and a disodium salt of impurity A: 2.2%.

The target compound was prepared according to the method of the above literatures, and the results were consistent with the literature results. Compared with the process provided in the present application, the yield was greatly reduced, and the post-processing and purification operations were cumbersome and not suitable for industrial scale-up production. The product obtained after purification does not meet the API quality requirements.

The above are only the preferred examples of the present application and are not intended to limit the present application. Any modifications, equivalent substitutions and improvements made within the spirit and principle of the present application should be included in the protection scope of the present application.

The invention claimed is:
1. A method for preparing Cangrelor tetrasodium salt, comprising the following steps:

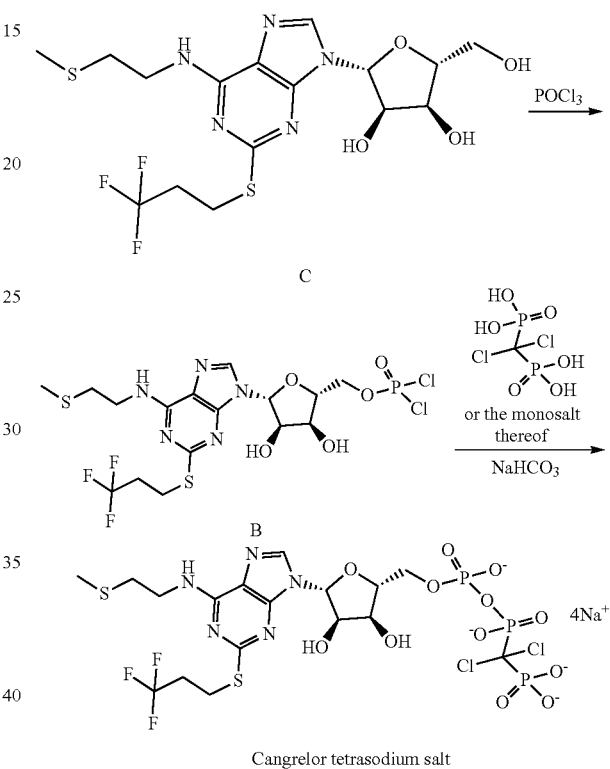

step (1), reacting a compound C with phosphorus oxychloride in an organic solvent to obtain a reaction solution containing a compound B;
step (2), reacting the reaction solution containing the compound B obtained in step (1) with clodronic acid or a monosalt thereof in the presence of an acid-binding agent, and then with sodium bicarbonate to obtain a reaction solution containing Cangrelor tetrasodium salt; and
step (3), obtaining Cangrelor tetrasodium salt from the reaction solution containing Cangrelor tetrasodium salt obtained in step (2);
wherein the step (3) is a step of separating and purifying the reaction solution containing Cangrelor tetrasodium salt obtained in step (2) by C18 silica gel column chromatography, eluting with an eluent, collecting the eluate of Cangrelor tetrasodium salt with a HPLC purity≥99.5% and lyophilizing to obtain Cangrelor tetrasodium salt.
2. The method according to claim 1, wherein in step (1) the organic solvent is selected from the group consisting of acetonitrile, triethyl phosphate, and trimethyl phosphate, or any combination thereof.

3. The method according to claim 1, wherein in step (1) the molar ratio of the compound C to the phosphorus oxychloride is 1:1 to 1:3.

4. The method according to claim 1, wherein in step (1) the compound C and phosphorus oxychloride are reacted in the presence of a base.

5. The method according to claim 1, wherein the reaction in step (1) is performed at a temperature of -30 to 20° C. for 1-24 h.

6. The method according to claim 1, wherein in step (2) the acid-binding agent is selected from the group consisting of triethylamine, tri-n-propylamine, tri-n-butylamine and N,N-diisopropylethylamine, or any combination thereof.

7. The method according to claim 1, wherein in step (2) the molar ratio of the compound C to the clodronic acid or the monosalt thereof is 1:1.1 to 1:3.5.

8. The method according to claim 1, wherein the monosalt of clodronic acid is selected from the group consisting of monosalt of tri-n-butylamine dichloromethylene diphosphate, monosodium salt of clodronic acid and monopotassium salt of clodronic acid, or any combination thereof.

9. The method according to claim 1, wherein in step (2) the molar ratio of the compound C to the sodium bicarbonate is 1:10-1:30.

10. The method according to claim 1, wherein in step (2) the reaction solution containing the compound B obtained in step (1) is reacted with the clodronic acid or the monosalt thereof at a temperature of -10 to 30° C. for 1-5 h.

11. The method according to claim 1, wherein in step (2) the reaction with the sodium bicarbonate is performed at a temperature of 10-40° C. for 10-40 h.

12. The method according to claim 1, wherein the step (3) is a step of separating and purifying the reaction solution containing Cangrelor tetrasodium salt obtained in step (2) by column chromatography once, eluting with an eluent to obtain an eluent of Cangrelor tetrasodium salt with a HPLC purity≥99.5%, lyophilizing to obtain Cangrelor tetrasodium salt.

13. The method according to claim 1, wherein the particle size of C18 silica gel filler is 20-150 microns.

14. The method according to claim 1, wherein in step (3) the eluent is selected from the group consisting of 0.1 v/v %-10 v/v % of aqueous methanol solution, 0.1 v/v-10 v/v % of aqueous acetonitrile solution and water.

15. The method according to claim 13, wherein the mass ratio of the C18 silica gel filler to the compound C is 35:1-130:1.

16. The method according to claim 4, wherein in step (1) the base is selected from the group consisting of 1,8-bis(dimethylamino)naphthalene, triethylamine, tri-n-propylamine, tri-n-butylamine, and diisopropylethylamine, or any combination thereof.

17. The method according to claim 4, wherein in step (1) the molar ratio of the compound C to the base is 1:0.1-1:2.

18. The method according to claim 1, wherein in step (2) the molar ratio of the compound C to the acid-binding agent is 1:2-1:8.

* * * * *